(12) United States Patent
Murray

(10) Patent No.: US 6,379,033 B1
(45) Date of Patent: Apr. 30, 2002

(54) DEVICE FOR FLOWING BONE CEMENT LIQUID INTO BONE CEMENT POWDER

(76) Inventor: William M. Murray, 2650 Spring Hill La., Enola, PA (US) 17025

( * ) Notice: Subject to any disclaimer, the term of this patent is extended or adjusted under 35 U.S.C. 154(b) by 0 days.

(21) Appl. No.: 09/580,898

(22) Filed: May 30, 2000

(51) Int. Cl.$^7$ ................................. B01F 15/02
(52) U.S. Cl. ..................... 366/139; 366/183.1
(58) Field of Search .............. 366/130, 139, 366/189, 341, 183.1; 206/219

(56) References Cited

U.S. PATENT DOCUMENTS

| | | | |
|---|---|---|---|
| 2,696,022 A | * | 12/1954 | Steinbock et al. |
| 4,808,184 A | | 2/1989 | Tepic |
| 5,051,482 A | | 9/1991 | Tepic |
| 5,071,040 A | | 12/1991 | Laptewicz, Jr. |
| 5,193,907 A | | 3/1993 | Faccioli et al. |
| 5,435,645 A | * | 7/1995 | Faccioli et al. |
| 5,443,182 A | | 8/1995 | Tanaka et al. |
| 5,549,380 A | | 8/1996 | Lidgren et al. |
| 5,551,778 A | | 9/1996 | Hauke et al. |
| 5,588,745 A | * | 12/1996 | Tanaka et al. |
| 5,876,116 A | | 3/1999 | Barker et al. |
| 5,975,751 A | * | 11/1999 | Earle |
| 6,017,349 A | | 1/2000 | Heller et al. |
| 6,024,480 A | * | 2/2000 | Seaton et al. |
| 6,042,262 A | * | 3/2000 | Hajianpour |
| 6,116,773 A | | 9/2000 | Murray |

FOREIGN PATENT DOCUMENTS

| | | | |
|---|---|---|---|
| WO | 88/03811 | * | 6/1988 |
| WO | 93/22041 | * | 11/1993 |
| WO | 94/26403 | * | 11/1994 |
| WO | 95/00240 | * | 1/1995 |
| WO | 98/38950 | | 9/1998 |

* cited by examiner

*Primary Examiner*—Charles E. Cooley
(74) *Attorney, Agent, or Firm*—Thomas Hooker, P.C.

(57) ABSTRACT

A bone cement mixer having a cartridge filled with bone cement powder and a monomer well for receiving monomer liquid to be flowed into the bone cement powder. The monomer liquid flows by gravity in a stream near the outer periphery of the bone cement powder. The stream penetrates the bone cement powder and forms a partial cylinder of monomer-rich powder essentially uniformly along the height of the bone cement powder. The powder and liquid are then mechanically mixed to form bone cement.

17 Claims, 3 Drawing Sheets

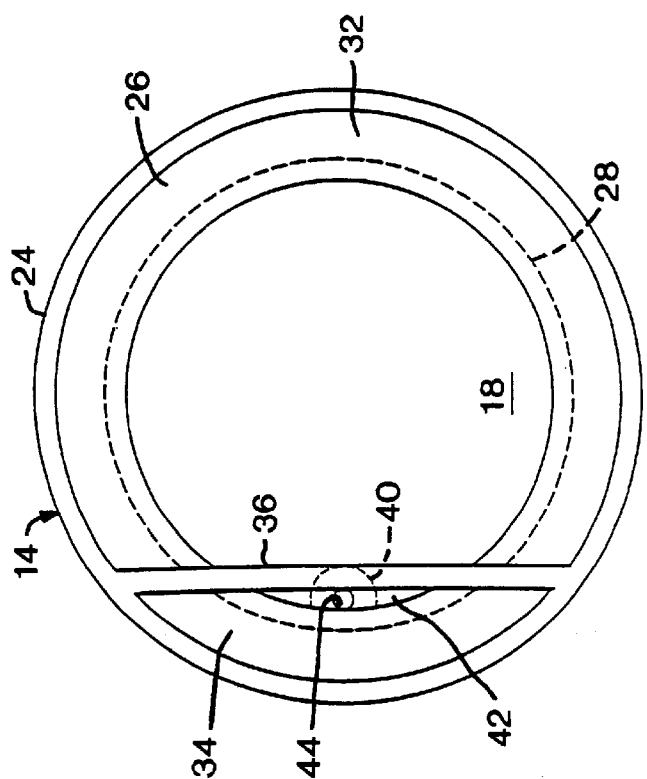
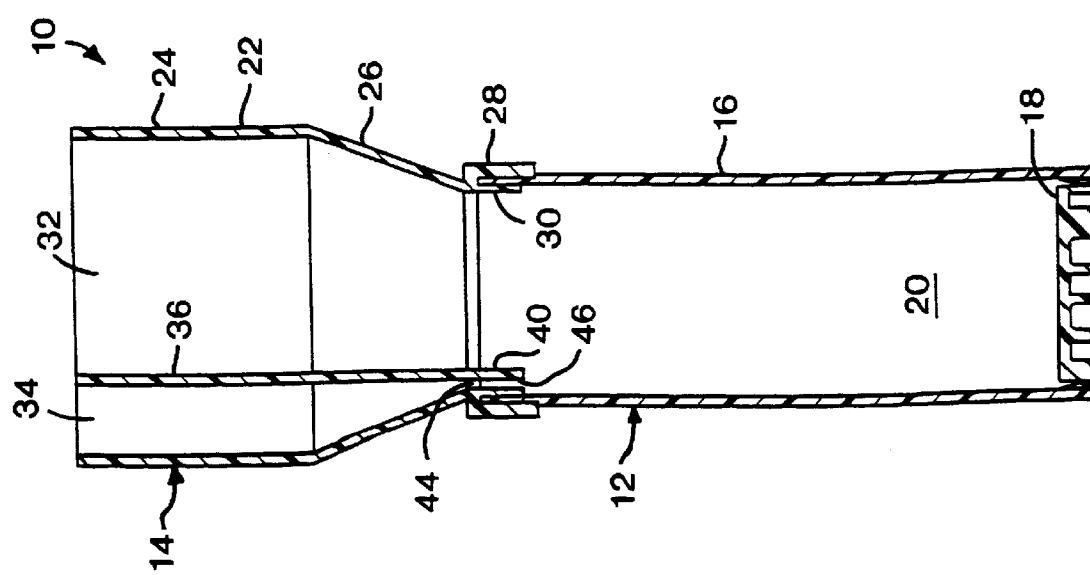

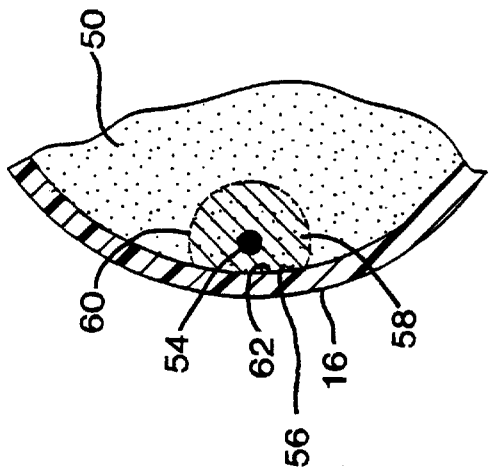
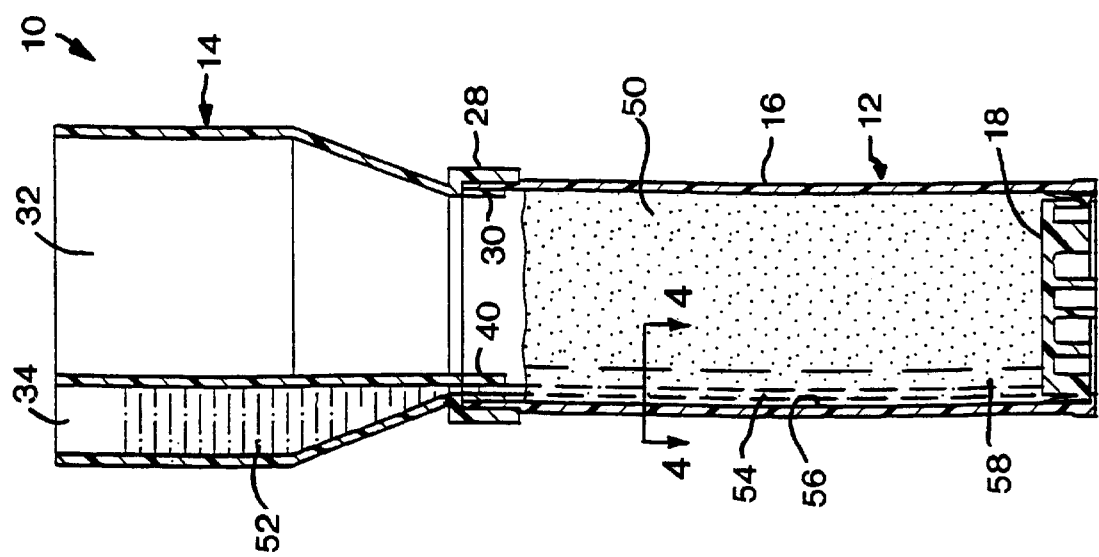

DEVICE FOR FLOWING BONE CEMENT LIQUID INTO BONE CEMENT POWDER

FIELD OF THE INVENTION

The invention relates to mixing of orthopedic bone cement, particularly to components and methods for mixing bone cement. The disclosed invention equally well relates to mixing of dental and other similar cements.

DESCRIPTION OF THE PRIOR ART

Cement used as a casting and grouting material to implant prosthetic devices into live bone is made from a very fine cement powder, typically polymethyl methacrylate, mixed with a monomer liquid, typically methyl methacrylate, to form a flowable bone cement mixture. Physical mixing of the dry cement powder and liquid is required in order to make a flowable cement. It is not sufficient to merely bring the liquid into contact with the cement powder because the liquid will not flow into the powder uniformly. During mixing the monomer liquid should be distributed equally throughout the mixture so that the mixture is uniform and possesses a uniform viscosity or thickness, consistent with the manufacturer's specifications.

Bone and dental cements are mixed using pre-packaged amounts or doses of dry bone cement powder and monomer liquid prepared by the manufacturer of the cement. The amounts of powder and liquid are measured to provide a cement mixture having desired properties when the powder and liquid are uniformly mixed together. Failure to mix the liquid and powder together uniformly means that part of the mixture contains an excess of monomer liquid and is runny and part of the mixture contains a deficiency of monomer liquid and is thicker than desired or, in some cases, retains unwetted dry powder.

It is quite important that the powder and monomer liquid be evenly mixed throughout the bone cement mixture. Bone cement with an excess of monomer liquid sets up slowly requiring increased operating room time and the risk of prosthesis displacement during protracted hardening or set-up of the cement. Such cement also possesses reduced strength. Further, during the increased set-up period there is a risk that blood or other bodily fluid will displace runny cement from adjacent the formed bone surface at an implant site and thereby weaken fixation between the hardened cement and bone.

Bone cement mixed with a deficiency of monomer liquid has a high viscosity and may be difficult to flow properly to the application site. This cement does not flow readily into the irregularities of a prepared bone surface to form a reliable joint. Further, bone cement with a deficiency of monomer liquid sets up relatively rapidly, reducing the already short amount of time available to the surgeon to perform an implantation procedure.

Bone cement is conventionally mixed in a bone cement mixer. The mixer has a funnel, a mixing chamber, a cover to close the chamber, and a mixing element or stirrer attached to the cover to mix the powder bone cement and monomer liquid together. Cement is typically mixed by placing the funnel on top of the mixing chamber, which may be the interior of a syringe cartridge, and pouring the required amount of bone cement powder through the funnel into the chamber. Monomer liquid is poured into the funnel and flows into the chamber on top of the powder. The funnel is removed and the cover is placed on the top of the mixing chamber. The cover closes the mixing chamber and inserts the stirrer into the cement powder. The stirrer is manually rotated in the chamber for a predetermined amount of time to mix the powder and liquid together and form a uniform, flowable bone cement. Insertion of the stirrer into the body of bone cement powder before monomer liquid is poured onto the powder compacts the powder and makes uniform mixing difficult.

It is important that the monomer liquid poured into the chamber be distributed in the powder to the extent that stirring will create a uniform, homogeneous bone cement mixture. The monomer liquid should preferably penetrate to the bottom of the powder body prior to stirring to ensure stirring will form a uniform mixture.

When the monomer liquid is poured on the powder, however, the liquid can form a puddle which wets the top of the powder. The wetted top layer of powder seals the powder and prevents air within the underlying powder from escaping. The liquid cannot penetrate deeply into the powder, because the liquid cannot displace the air within the powder. Hence powder at the bottom of the powder body remains dry. Stirring then will not uniformly mix the liquid and powder. Some powder may remain totally dry while other powder may be mixed with an excess of monomer liquid.

The just described problem of achieving desirable monomer liquid distribution prior to stirring is well recognized. This is particularly a problem where the powder placed in the chamber forms a tall column of powder, such as when the height of the powder column is greater than its diameter. This is typically the case when the cement is mixed in a tall, narrow bone cement cartridge of the type used to extrude mixed cement to an application site. The taller the column, the more difficult it is for the monomer liquid to penetrate to the bottom of the powder.

A conventional method for achieving the desired penetration of monomer liquid into the powder column when using a syringe cylinder as a mixing chamber requires pouring cement powder and monomer liquid alternately, in small amounts, into the chamber until the total amounts to be mixed have been poured into the chamber. The powder and liquid are then mixed. While this method can achieve improved uniformity of monomer liquid distribution, it has serious disadvantages. First, it consumes valuable extra time, and the duration of the time consumed results in a mixture which is not homogeneous in terms of the starting time of its mixing and, hence, its setting time. Second, the layering of monomer liquid which results from this method can isolate regions of loosely packed dry powder containing air which can form air inclusions in the mixed cement.

Other methods for achieving the desired penetration of monomer liquid into the powder column when using a syringe cylinder as a mixing chamber are known. Tilting or inclining the cylinder immediately before pouring the monomer liquid into the chamber promotes monomer liquid flow to the bottom of the powder. However, the powder cannot be compacted by prior handling or storage. Alternatively, a stream of monomer liquid can be flowed into the powder at high speed. This requires a mixer of relatively large size and complexity.

Thus, there is a need for an improved bone cement mixer and method which distributes monomer liquid poured on a column of bone powder in a tall, narrow bone cement mixing chamber, such as a bone cement cartridge, so that stirring will create a uniform, homogeneous bone cement mixture.

SUMMARY OF THE INVENTION

The invention relates to bone cement mixers in which bone cement liquid is flowed into dry bone cement powder, components and methods for mixing bone cement powder and monomer liquid wherein the monomer liquid poured on the bone cement powder prior to mixing is distributed through the column of bone cement to the extent that stirring will create a uniform, homogeneous bone cement mixture.

The cement is preferably mixed in a high, narrow bone cement cartridge. The bone cement powder is poured into the cartridge and forms a body of powder surrounded by the wall of the cartridge. A stream of monomer liquid is then flowed by gravity through a nozzle that aims down onto the top of the body of bone cement powder close to the cartridge wall. Monomer liquid from the gravity stream impacts the bone cement powder and is absorbed into the powder surrounding the stream. The liquid absorbed into the powder flows outwardly from the stream and attempts to form a cylinder of monomer-rich powder surrounding the stream. The remainder of the powder remains dry prior to mixing.

The nozzle is located so that the stream of monomer liquid is spaced a short distance from the wall of the cartridge to impact near the outer periphery of the body of powder. The stream is spaced sufficiently close to the outer periphery of the powder body such that some of the absorbed liquid flowing outwardly from the stream reaches the outer periphery of the powder body and is blocked by the wall. The wall prevents further outward flow of the liquid and prevents a cylinder of monomer-rich powder from surrounding the stream. Instead, a partial cylinder of monomer-rich powder forms against the wall and surrounds the stream. The partial cylinder of monomer-rich powder extends to the bottom of the powder.

Flowing the stream of monomer liquid near the outer periphery of the powder column to form a partial cylinder of monomer-rich powder enables a gravity-flowed stream to penetrate to the bottom of the powder without forming a puddle of bone cement liquid on top of the bone cement powder. The bone cement liquid is distributed essentially uniformly along the height of the bone cement powder column while maintaining the bone cement powder in the column remote from the stream dry.

After flowing the monomer liquid in the column, the bone cement powder and monomer liquid are mixed conventionally to form bone cement having an essentially uniform viscosity. The bone cement cartridge is then placed in a conventional bone cement gun for extrusion to an application site.

In a preferred embodiment, the nozzle is located below a liquid well that has an open upper end for receiving monomer liquid. An outlet passage flows the liquid in the well by gravity to the nozzle. The nozzle extends downwardly and includes a vertical flow passage sized to flow a stream with sufficient velocity to penetrate to the bottom of the powder body. The cartridge need not be evacuated prior to flowing monomer liquid into the powder.

Other objects and features of the invention will become apparent as the description proceeds, especially when taken in conjunction with the accompanying drawings illustrating the invention, of which there are three sheets and two embodiments.

DESCRIPTION OF THE DRAWINGS

FIG. 1 is a vertical sectional view of a first embodiment funnel in accordance with the present invention mounted on top of an empty bone cement cartridge;

FIG. 2 is a top view of the funnel and cartridge shown in FIG. 1;

FIG. 3 is similar to FIG. 1 and illustrates discharge of monomer liquid into bone cement powder in the cartridge;

FIG. 4 is a partial sectional view taken along line 4—4 shown in FIG. 3;

DESCRIPTION OF THE PREFERRED EMBODIMENTS

Figure 6:
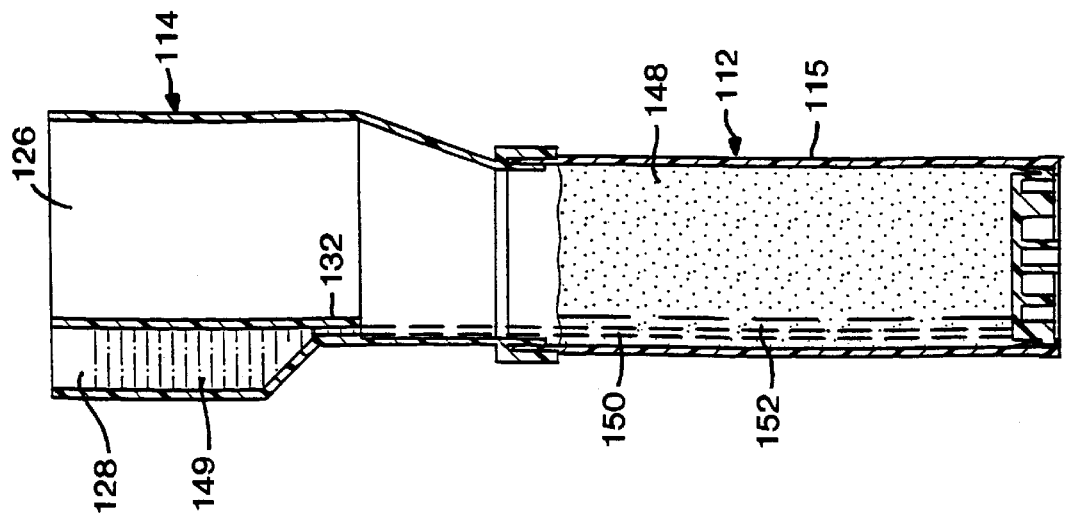
FIG. 6 is similar to FIG. 5 and illustrates discharge of monomer liquid into bone cement powder in the cartridge.

FIGS. 1 and 2 illustrate a device 10 in accordance with the present invention for pouring a bone cement liquid into bone cement powder to form liquid bone cement. The device 10 includes a conventional syringe or bone cement cartridge 12 for mixing the monomer liquid and bone cement powder and a funnel 14 for pouring the monomer liquid and bone cement powder into the cartridge 12 prior to mixing. The cartridge 12 includes a plastic cylindrical body 16 and a piston 18 closing the lower end of the body. The body 16 and piston 18 define a tall, narrow mixing chamber 20. The upper end of the body is open to receive monomer liquid and bone cement powder into the mixing chamber 20.

The funnel 14 includes a tubular body 22 having an upper cylindrical intake portion 24 and a lower conical discharge portion 26. A collar 28 is provided on the lower end of the discharge portion 26 to removably mount the funnel 14 on the upper end of the cartridge body 16. The collar 28 includes an internal circumferential lip 30 which surrounds the top of the cartridge body 16.and extends a short distance down into the interior of the body. Lip 30 guides powder into the cartridge and prevents leakage from the assembled cartridge and collar.

The funnel 14 is divided into bone cement powder delivery passage 32 and a monomer well 34 by an off-center vertical partition wall 36 that extends across the interior of body 22. The wall 36 extends downwardly from the top of the funnel 14 to the collar 28. The passage 32 is open at the top and bottom of the funnel and flows dry bone cement powder into the mixing chamber 20. The smaller well 34 flows monomer liquid through the funnel 14 and onto the bone cement powder in the mixing chamber.

The monomer liquid well or chamber 34 is open at its upper end for holding monomer liquid poured into the well. The well 34 is connected to a nozzle 40 at the bottom of the well that discharges the liquid from the well. As shown in FIG. 1, the nozzle 40 is beneath the well and is aimed to flow liquid vertically into the mixing chamber 20 when the funnel 14 is placed on the cartridge 12.

The monomer well or chamber 34 includes a small horizontal bottom wall 42 that extends from the lower end of the partition wall 36 to the funnel body 22. The funnel body 22, partition wall 36 and lower wall 42 define the liquid well 34. A vertical outlet passage 44 extends down through the lower wall 42 and connects the well 34 to a vertical flow passage 46 in the nozzle 40.

The nozzle 40 is aimed from the lower wall 42 along the inner collar lip 30. The flow passage 46 is immediately adjacent the inner collar lip 30 to position the flow passage near the inner wall of the cartridge body 16 when the funnel 14 is placed on the cartridge 12. See FIG. 2. The lower end of the nozzle 40 is even with the lower end of the circumferential lip 30.

Bone cement is marketed by manufacturers in prepackaged amounts or doses which are mixed together by users to make a single batch of bone cement. Typically fine polymethyl methacrylate powder is packaged in forty gram doses and liquid methyl methacrylate monomer liquid is sealed in glass ampules in 20 milliliter doses. Device 10 may be used to mix one, two or three doses of bone cement powder and monomer liquid, depending upon the volume of cement required for a particular application.

FIGS. 3 and 4 illustrate operation of bone cement mixer 10. Prior to mixing bone cement, any cover is removed from the upper end of the bone cement, cartridge 12. The funnel 14 is mounted above the cartridge 12 with the funnel collar lip 30 sealing the upper end of the cartridge body 16. The monomer well 34 is above the cartridge 12 with the nozzle 40 extending into the cartridge mixing chamber 20.

The cartridge 12 is filled with an appropriate member of doses of bone cement powder by pouring the bone cement powder into funnel powder passage 32. One, two or three doses of bone cement powder may be poured as appropriate. The bone cement powder flows into the cartridge body 16 and forms a body or column of bone cement powder in the mixing chamber 20. FIG. 3 illustrates a body of bone cement powder 50 in the cartridge. The height of the powder body 50 is greater than its width.

The appropriate number of doses of monomer liquid for mixing with the bone cement powder in the cartridge are then poured into open monomer well 34. AS each dose is poured into the well 34, the monomer liquid 52 in the well flows by gravity down outlet passage 44 and out the flow passage 46 in nozzle 40 in a small diameter, vertical stream 54. The stream 54 discharges from the nozzle 40 in the plane of the lower end of the collar lip 30 so that the lip 30 does not interfere with the flow of the stream 54. The stream 54 flows down onto the bone cement body 50 in the cartridge near the outer periphery of the body 50 and a short distance inwardly from the inside of the tubular body 16.

The monomer stream 54 penetrates the height of the bone cement body 50 and is absorbed into the bone cement powder in the body. Bone cement liquid does not puddle on the top of the bone cement powder. Monomer liquid is absorbed into the bone cement powder relatively uniformly along the height of the body. Uniform distribution of monomer liquid along the body facilitates mixing of the monomer liquid into the bone cement powder. The person operating mixer 10 can observe the level of monomer liquid in well 48 and determine when the last dose of monomer liquid has been flowed into the cement powder.

The leading end of the monomer stream 54 hits the bone cement powder in powder body 50 and is absorbed into the powder. The absorbed liquid flows outwardly from the stream and attempts to form a cylindrical column of wetted powder having a substantially circular cross-section surrounding the stream 54. However, the stream 54 is sufficiently close to the outer periphery of the powder body 50 such that some of the absorbed liquid flowing from the stream 54 reaches the outer periphery of the powder body and is blocked by an inner wall portion 56 of the cartridge body 16. The wall portion 56 prevents further outward flow of the liquid and prevents a circular cylinder of monomer-rich powder from forming around the stream 54. Instead, a partially circular cylinder 58 of monomer-rich powder forms at the outer periphery of the powder body 50 against the inner wall portion 56. The outer periphery of the partial cylinder 58 includes a substantially circular cylindrical portion 60 that extends inwardly from the cartridge body 16 and a cut-off portion 62 against the inner wall portion 56 of the cartridge body 16. The shape of the cut-off portion 62 is defined by the shape of the inner wall portion 56. The partial cylinder 58 of monomer-rich powder surrounds the stream 54 and extends to the bottom of the powder body 50.

The powder in the powder body 50 away from the partial cylinder 58 remains dry. The powder dissolves into the monomer liquid as monomer liquid wicks outwardly into the surrounding dry powder.

Because the inner wall portion 56 of the cartridge body 16 obstructs outward flow of the monomer liquid and prevents a complete cylinder of monomer-rich powder from forming around the stream 54, the cross sectional area of the partial cylinder 58 is less than if a complete cylinder of monomer-rich powder formed around the stream 54. The monomer liquid in the partial cylinder 58 is thus concentrated in a smaller volume and can more easily penetrate the body of bone cement powder. The eccentric location of the partial cylinder 58 of monomer-rich powder within the powder body 50 ensures that a portion of the powder body 50 will remain unwetted at all levels of its vertical extent.

After all the monomer liquid has been flowed into the bone cement powder, the funnel 14 is removed and a stirrer (not shown) is inserted into the body of cement powder in a conventional manner to mix the powder and liquid together. The mixed liquid and powder form a uniform, flowable bone cement. The cartridge 12 is then placed in a conventional bone cement gun (not shown) to extrude the flowable bone cement to an application site. The mixer may be evacuated before mixing.

In other possible embodiments of the device 10, the bone cement cartridge 12 may be filled with an appropriate member of doses of bone cement powder by a manufacturer and then sealed for shipment to a user. In such embodiments the step of pouring bone cement powder through funnel 14 and into the cartridge 12 may be omitted.

Bone cement mixer 10 gravity flows monomer liquid from a monomer reservoir or well through a nozzle. The nozzle is located near the outer periphery of a bone cement body to form a partial cylinder of liquid-rich bone cement powder extending along the outer periphery of the bone cement body against the inner wall of the mixing chamber. The nozzle is preferably located so that the stream of monomer liquid is not more than about 0.25 inches from the outer periphery of the powder body.

During flowing of monomer liquid into the bone cement powder the monomer stream 54 gravity flows at a speed dependent upon the cross sectional area of the nozzle flow passage. In one test a 20 milliliter dose of monomer liquid flowed through a cylindrical nozzle having an interior diameter of about 0.075 inch in about 11 seconds. This is a sufficiently rapid flow to not slow the mixing process. The flow passage in the nozzle had a cross sectional area of about 0.005 square inches. However, nozzles having a larger or smaller cross sectional area than the tested nozzle may be used and the bone cement liquid may be flowed into the cement powder in a shorter or longer time.

The information given concerning the size of nozzle flow passage and the duration for flowing the monomer liquid into bone cement powder stated above are exemplary and are not meant to limit the invention. In any event, this information may not be correct for all bone cements.

Figure 5:
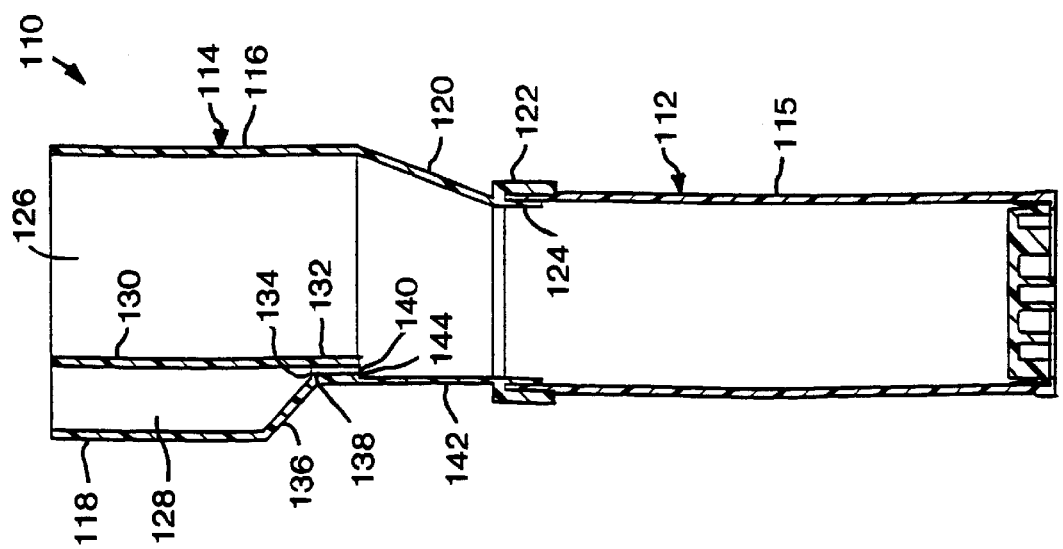
FIG. 5 is a vertical sectional view of a second embodiment funnel in accordance with the present invention mounted on top of an empty bone cement cartridge.

In device 10 the nozzle 40 is within the cartridge 12 and may contact the bone cement powder in the mixing chamber 20 when pouring the monomer liquid. FIG. 5 illustrates a second embodiment device 110 in accordance with the present invention in which the nozzle is above the cartridge when pouring the monomer liquid.

The device 110 includes a conventional bone cement cartridge 112, like cartridge 12, and a funnel 114 for pouring the monomer liquid and bone cement powder into the cartridge 112 prior to mixing. The cartridge 112 includes a tubular body 115. The funnel 114 includes a tubular body 116 having a generally cylindrical upper intake portion 118 and an open lower discharge portion 120. A cylindrical collar 122, like collar 28, is formed on the lower end of discharge portion 120 with an inner sealing lip 124.

A bone cement powder delivery passage 126 and a monomer liquid well or chamber 128, similar to passage 32 and well 34 of device 10, are separated by an off-center vertical partition wall 130. The partition wall 130 is spaced a substantial distance above the collar 122.

The monomer well 128 is connected to a discharge nozzle 132. As shown in FIG. 5, the nozzle 132 is beneath the monomer well 128 and is aimed to flow liquid vertically into the cartridge 112 when the funnel 114 is placed on the cartridge. The monomer well 128 and the nozzle 132 are spaced a substantial distance above the lower collar 122.

The monomer well 128 includes a bottom horizontal wall 134 that extends from the lower end of the partition wall 130 across to a sloped side wall portion 136 of the funnel body 116. A vertical outlet passage 138 extends through the lower wall 134 and connects the monomer well 128 to a vertical flow passage 140 in the nozzle 132.

The nozzle 132 extends downwardly from the lower wall 134 along a partially cylindrical side wall portion 142 of the funnel discharge portion 120. The side wall portion 142 extends from the well side wall portion 136 to the funnel collar 122. The inner diameter of the side wall portion 142 is the same as the inner diameter of the collar lip 124. The lower end of the nozzle 132 is spaced a substantial distance above the funnel collar 122. The flow passage 140 is spaced inwardly a very short distance from the side wall 142 by a thickened nozzle wall 144 to position the flow passage near the side wall portion 142 while aiming the flow passage near the inside of the sealing lip 124.

FIG. 6 illustrates operation of the device 110. The cartridge 112 is filled with an appropriate number of doses of bone cement powder to form a body or column of bone cement powder 148 in the cartridge. When the funnel 114 is mounted on the cartridge 112, the nozzle 132 is spaced above the cartridge 112 and would not contact the bone cement powder in the cartridge.

The appropriate number of doses of monomer liquid for mixing with the bone cement powder in the cartridge are poured into open monomer well 128. As each dose is poured into the well 128, the monomer liquid 149 in the well flows by gravity down outlet passage 138 and out the flow passage 140 in nozzle 132 in a vertical stream 150. The stream 150 discharges from the nozzle 132 and flows adjacent to the side wall portion 142 and the sealing lip 124 before entering the cartridge 112.

The stream 150 flows down onto the bone cement powder body 148 in the cartridge 112 near the outer periphery of the powder body 148 and a short distance inwardly from the inside of the cartridge body 115. The monomer stream 150 forms a partial cylinder 152 of monomer-rich powder, similar to partial cylinder 58, against the cartridge body 115. The partial cylinder 152 of monomer-rich powder surrounds the stream 150 and extends to the bottom of the powder body 148. Monomer liquid is essentially uniformly distributed along the height of the bone cement powder column.

The funnel 114 is then removed and a stirrer is inserted into the body of cement powder in a conventional manner to mix the powder and liquid together. The cartridge may be evacuated before mixing. The mixed liquid and powder form a uniform, flowable bone cement. The cartridge 112 is then placed in a conventional bone cement gun (not shown) to extrude the flowable bone cement to an application site.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention is:

1. A device for flowing bone cement liquid into dry bone cement powder prior to mixing the bone cement liquid and the bone cement powder together to form liquid bone cement, the device comprising:

(a) a circumferential body open at the top of the body, and a member closing the bottom of the body, the body and member defining a bone cement mixing chamber; and (b) a funnel on the top of the body above the mixing chamber, the funnel including a circumferential wall extending around the circumferential body and forming a vertical extension of the circumferential body, a partition wall extending across the interior of the circumferential wall, said partition wall offset to one side of the center of the funnel to form a relatively large bone cement delivery passage and a relatively small bone cement liquid well, said passage open at the top and bottom of the funnel to permit gravity flow of dry bone cement powder through the funnel and into the mixing chamber, said well open at the top of the funnel, and a small bone cement liquid discharge passage extending through the bottom of the well and opening into the mixing chamber, the passage located sufficiently close to the interior surface of the circumferential body so that bone cement liquid flows by gravity from the liquid well, through the discharge passage and down into the mixing chamber in a stream extending along and closely adjacent to the circumferential body without touching the body; wherein an appropriate number of doses of dry bone cement powder poured into the delivery passage gravity flow into the mixing chamber to form a body of dry bone cement powder under the discharge passage, an appropriate number of doses of bone cement liquid poured into the bone cement liquid well gravity flow out of the well through the discharge passage and down into the body of powder in the mixing chamber in a penetrating gravity stream extending through the height of the body of powder, and bone cement liquid is absorbed outwardly from the stream into dry bone cement powder to form a partial cylindrical column of wetted powder surrounding the stream and engaging the adjacent interior surface of the circumferential body without puddling on the top of the powder so that the bone cement liquid is substantially uniformly distributed along the height of the body of bone cement powder.

2. The device as in claim 1 wherein the discharge passage is located within about 0.25 inch from the circumferential body.

3. The device as in claim 2 wherein the discharge passage has a diameter of about 0.075 inch.

4. The device as in claim 1 wherein the funnel includes means located around the inner circumference of the top of the circumferential body for guiding dry bone cement powder into the chamber, and structure on the bottom of the funnel overlying the top of the circumferential body.

5. The device as in claim 4 wherein said means comprises a lip extending around the inside of the top of the circumferential body and said funnel includes a collar extending around the outside of the circumferential body.

6. The device as in claim 1 wherein the funnel includes a lower discharge portion and the discharge passage is above the lower discharge portion.

7. The device as in claim 1 wherein the circumferential body is cylindrical and the member comprises a piston movable along the cylindrical body.

8. The device as in claim 7 wherein the discharge passage has a diameter of about 0.075 inch.

9. A device for flowing bone cement liquid into dry bone cement powder prior to mixing the bone cement liquid and bone cement powder together to form liquid bone cement, the device comprising:

(a) a mixing chamber having a circumferential body open at the top of the chamber; bone cement powder in the mixing chamber;

(b) a funnel on the top of the mixing chamber, the funnel including a bone cement liquid chamber having an open top, and bone cement liquid discharge means extending through the bottom of the liquid chamber for gravity flowing bone cement liquid from the liquid chamber down into the bone cement powder in the mixing chamber along and closely adjacent to the circumferential body in a bone cement penetrating stream without puddling bone cement liquid on the top of bone cement powder wherein the bone cement powder in the mixing chamber is penetrated by the stream and the bone cement liquid in the stream is absorbed outwardly of the stream into the powder; and (c) a partial cylindrical body of wetted bone cement powder in the mixing chamber under the bone cement liquid discharge means, the partial cylindrical body having a first portion in contact with the circumferential body of the mixing chamber and a second partial cylindrical portion contacting the bone cement powder, said wetted bone cement powder including bone cement liquid distributed essentially uniformly along the height of the partial cylindrical body.

10. The device as in claim 9 wherein the discharge means is located no more than about 0.5 inch from the circumferential body.

11. The device as in claim 10 wherein the liquid discharge means comprises a passage having a diameter of about 0.075 inch.

12. The device as in claim 11 wherein the funnel includes a bone cement delivery passage located above the mixing chamber, the bone cement delivery passage being larger than the liquid chamber.

13. The device as in claim 9 wherein the funnel includes a lower discharge portion and the liquid discharge means is above the lower discharge portion.

14. The device as in claim 9 wherein the mixing chamber comprises a cylindrical member and a piston movable along the cylindrical member.

15. A device for mixing a bone cement liquid with a bone cement powder, the device comprising:

(a) a mixing chamber having a circumferential wall and a bottom; bone cement powder in the mixing chamber;

(b) an open gravity flow cement liquid chamber located above the mixing chamber;

(c) nozzle means at the bottom of the liquid chamber located above the mixing chamber and adjacent to the mixing chamber wall for gravity flow of a penetrating stream of bone cement liquid into the bone cement powder in the mixing chamber without forming a puddle of bone cement liquid on the top of the powder; and (d) a partial cylindrical body of bone cement powder wetted by the bone cement liquid, the body located in the mixing chamber and under the nozzle means, the partial wetted cylindrical body having a first portion in contact with the circumferential wall of the mixing chamber and a second partial cylindrical portion contacting the bone cement powder, said wetted bone cement powder including bone cement liquid distributed essentially uniformly along the height of the body of dry bone cement powder.

16. The device as in claim 15 wherein the nozzle means is located within about 0.25 inch from the mixing chamber circumferential wall.

17. The device as in claim 16 wherein the nozzle means includes a passage having a diameter of about 0.075 inch.

\* \* \* \* \*